(12) United States Patent
Land et al.

(10) Patent No.: US 8,678,980 B2
(45) Date of Patent: Mar. 25, 2014

(54) LOW PROFILE HAND-EXTENSION/FLEXION DEVICE

(71) Applicant: The Johns Hopkins University, Baltimore, MD (US)

(72) Inventors: Edward M. Land, Owings Mills, MD (US); H. Lee Mantelmacher, Owings Mills, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 13/705,673

(22) Filed: Dec. 5, 2012

(65) Prior Publication Data

US 2013/0096477 A1 Apr. 18, 2013

Related U.S. Application Data

(62) Division of application No. 13/178,083, filed on Jul. 7, 2011, now Pat. No. 8,348,810.

(60) Provisional application No. 61/382,627, filed on Sep. 14, 2010.

(51) Int. Cl.
*A63B 23/16* (2006.01)
*A61F 5/00* (2006.01)

(52) U.S. Cl.
USPC .................................. 482/47; 602/5

(58) Field of Classification Search
USPC ............... 482/44–48, 124; 601/5, 33–35, 40; 602/5; 2/159–160
See application file for complete search history.

(56) References Cited

U.S. PATENT DOCUMENTS

| 494,197 | A | * | 3/1893 | Hall | 482/48 |
| 3,347,547 | A | * | 10/1967 | Hynes | 482/47 |
| 3,944,220 | A | * | 3/1976 | Fasano | 482/47 |
| 4,766,612 | A | * | 8/1988 | Patton, Sr. | 2/16 |
| 4,830,360 | A | * | 5/1989 | Carr, Jr. | 482/47 |
| 5,453,064 | A | * | 9/1995 | Williams, Jr. | 482/47 |
| 5,697,103 | A | * | 12/1997 | Wiggins | 2/159 |
| 5,865,770 | A | * | 2/1999 | Schectman | 601/23 |
| 5,925,008 | A | * | 7/1999 | Douglas | 602/22 |
| 7,234,172 | B1 | * | 6/2007 | Hoelscher | 2/161.1 |
| 7,406,720 | B2 | * | 8/2008 | Hoelscher | 2/161.1 |
| 7,601,130 | B2 | * | 10/2009 | Farrell et al. | 602/20 |
| 8,348,810 | B2 | * | 1/2013 | Land et al. | 482/47 |
| 2003/0073939 | A1 | * | 4/2003 | Taylor et al. | 601/40 |
| 2003/0195093 | A1 | * | 10/2003 | White | 482/124 |

(Continued)

*Primary Examiner* — Stephen Crow
(74) *Attorney, Agent, or Firm* — Johns Hopkins Technology Transfer (57) ABSTRACT

A movement device for flexing and/or straightening a joint of a user includes a first anchor element adapted to be positioned adjacent a jointed appendage of a user at a first position. A second anchor element is adapted to be positioned about the jointed appendage at a second position, wherein the jointed appendage is located between the first anchor element and the second anchor element. A spring member is positioned between the first and second anchor elements wherein the spring member is fixedly secured to the second anchor element and moveable through the first anchor element to thereby allow the spring member to bend about a joint of the appendage when said appendage is flexed. The spring member is configured to exert bending forces in opposition to working muscles of the user to straighten or flex the joint of the appendage. To minimize discomfort, an intermediary support device is disposed between the first anchor element and the second anchor element which prevents the spring member from contacting the joint of the user.

1 Claim, 6 Drawing Sheets

(56) References Cited

U.S. PATENT DOCUMENTS

| | | |
|---|---|---|
| 2006/0094989 A1* | 5/2006 | Scott et al. .................. 601/5 |
| 2006/0211964 A1* | 9/2006 | Farrell et al. ................ 602/5 |
| 2009/0196463 A1* | 8/2009 | Kuniz et al. ................ 382/107 |
| 2009/0271912 A1* | 11/2009 | Jaunault et al. .............. 2/160 |
| 2010/0234182 A1* | 9/2010 | Hoffman et al. ............. 482/8 |

* cited by examiner

LOW PROFILE HAND-EXTENSION/FLEXION DEVICE

CROSS-REFERENCE TO RELATED APPLICATIONS

This application is a divisional of U.S. patent application Ser. No. 13/178,083 filed Jul. 07, 2011 which claims the benefit of U.S. Provisional Patent Application Ser. No. 61/382,627 filed on Sep. 14, 2010, the content of each of the aforementioned applications are herein incorporated by reference in their entirety.

REFERENCE TO RELATED APPLICATIONS

This application claims the benefit of U.S. Provisional Patent Application No. 61/382,627, filed on Sep. 14, 2010, which is hereby incorporated by reference for all purposes as if fully set forth herein.

FIELD OF THE INVENTION

The present invention pertains to a movement device. More particularly, the present invention pertains to a movement device for hand extension and flexion.

BACKGROUND OF THE INVENTION

Millions of Americans, including stroke victims, have lost the ability to open a partially paralyzed, clenched fist. Inability to open the hand precludes functional use of that hand and limits the functional use of the limb. A significant number of stroke survivors retain their ability to grasp with a varying degree of grip strength due in part to disuse brought about by the stroke. These individuals lack the ability to re-open their affected hand volitionally in order to release or accommodate objects. Many of these individuals, due to the nature of how a stroke affects the limbs, still are able to effectively control the shoulder and elbow. Consequently, the isolated loss of adequate finger motion imparts significant disability to stroke victims who otherwise should be able to functionally use their impaired upper extremity.

Most products currently available are bulky and difficult to use. Similarly, many devices are designed as therapeutic aides to permit exercising the fingers with the goal of recovery from an injury or act as a splint. In some cases, these devices measure the forces and motions of each finger providing valuable therapeutic information. These devices, in general, are not intended to assist the user in opening or closing the hand for the purpose of regaining utility of the limb.

Existing assistive devices use intrusive metal cables or employ awkward, oversized, exoskeleton housings for each finger and in some cases use small but heavy motors. Most of these devices have been designed to provide passive stretching of the fingers over a long period of time, although some, despite their bulky size, can be used to facilitate functional use of the hand in individuals who retain some grasp ability but lack hand-extension. In one such design, the suspension cable (bridge-like) passive-opening device can only be worn at night to stretch the ligaments and must be worn in a fixed position to permit the fingers to stretch. Many prior art designs employ complex mechanical structures that are both difficult to manufacture, use, clean, and are failure prone. Considering that no two hands are alike, rigid mechanical structures employing tensioning cables and supporting scaffolds are difficult, if not painful, to adjust and readjust to fit the hand.

Accordingly, there is a need in the art for a simple, convenient, mechanically robust movement device to allow opening and/or closing the fingers of hands of stroke victims and others who have lost all or part of the ability to move their fingers.

SUMMARY

According to a first aspect of the present invention, a movement device comprises a first anchor element adapted to be positioned adjacent a jointed appendage of a user at a first position, a second anchor element adapted to be positioned about the jointed appendage at a second position, wherein the jointed appendage is located between the first anchor element and the second anchor element. A spring member is positioned between the first and second anchor elements. The spring member is fixedly secured to the second anchor element and moveable through the first anchor element to thereby allow the spring member to bend about a joint of the appendage when the appendage is flexed. The spring member configured to exert bending forces in opposition to working muscles of the user to straighten or flex the joint of the appendage. An intermediary support device is disposed between the first anchor element and the second anchor element so as to prevent the spring member from contacting the joint of the user.

According to a second aspect of the present invention, hand extension/flexion device comprises a glove body for positioning around a user's affected hand. The glove body includes at least one finger portion for positioning about a finger and a hand portion for positioning around a top portion of the hand. At least one spring member is adapted to be positioned above the finger portion of the glove body and anchored at a tip of the finger portion of the glove with a second anchor element. The spring member is moveable through a first anchor element to thereby allow the spring member to bend about a joint of a finger of a user when the finger is flexed. The spring member is configured to exert bending forces in opposition to working muscles of the user to straighten or flex joints of the finger. An intermediary support device disposed between the first anchor element and the second anchor element so as to prevent the spring member from contacting the knuckles of the user.

According to a third aspect, a disposable glove for use in a hand extension/flexion device comprises a glove body for positioning around a hand of a user, a series of pads affixed to the surface of at least one finger portion of the glove body. The pads are positioned between joints of the finger. A channel is disposed about the pad, the channel for housing a spring member adapted to exert bending forces in opposition to working muscles of the user to straighten or flex joints of the finger. An anchor element for receiving a proximal end of the spring member.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

The presently disclosed subject matter now will be described more fully hereinafter with reference to the accompanying Drawings, in which some, but not all embodiments of the inventions are shown. Like numbers refer to like elements throughout. The presently disclosed subject matter may be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

The present invention pertains to a passive device. The term "passive" applies to embodiments that rely on the elastic properties of bent or stretched materials to apply forces, without requiring heat, electricity or other means to change the shape or mechanical properties of the material. Examples of materials include but are not limited to super memory alloys (SMAs) such as Nitinol (NiTi), titanium, stainless steel, carbon fiber, carbon nano-fiber, a carbon impregnated polymer based material, and/or other super-elastic materials. However, it should be understood that the present invention may also use, in combination with passive materials, "active" materials. The term "active" refers to embodiments using materials such as SMAs, electroactive polymers (EAPs) or other materials that can be activated by heat, electricity, or other means to change shape or mechanical properties and thereby apply the required forces. Combinations of active and passive materials can be used when beneficial to the needs of the user.

Figure 1A:
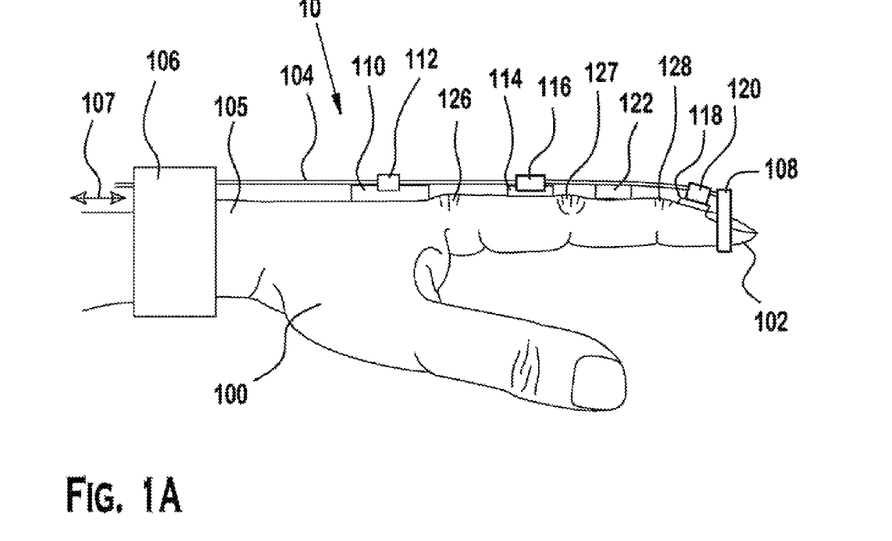
FIG. 1A illustrates a side elevational view of an exemplary product according to the features of the present invention with the fingers in an extended or straightened position.
Figure 1B:
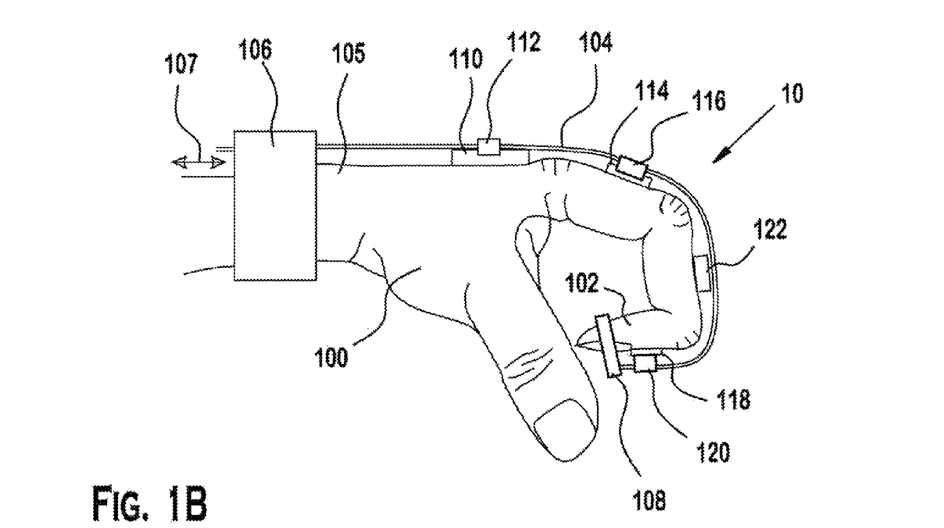
FIG. 1B illustrates a side elevational view of an exemplary product according to the features of the present invention with the fingers in a flexed position.

With reference to FIGS. 1A and 1B, an exemplary embodiment of the movement device is illustrated. While the exemplary movement device 10 is shown in connection with a hand 100, it should be understood that the movement device 10 of the present invention can be used with any joint, including but not limited to, the wrist, elbow, knee, feet, and toes. In addition, while only one finger 102 is illustrated in the FIGS. 1A and 1B, it should be understood that features of the movement device may extend to one, some, or all fingers and/or thumb, depending upon application. That is, each and any number of fingers and thumb may be used in the movement device, which pertains equally to either the right or left hand, depending upon the needs of the user.

With reference in particular to FIG. 1A, the movement device 10 of the present invention includes a spring member 104 adapted to bend about a joint of the appendage when the appendage is flexed. Preferably, the spring member 104 is parallel or is appropriately disposed with respect to each appendage so that they can only bend in a single plane, and in some embodiments when used with a hand and at certain locations, corresponding to the desired movement at each interphalangeal and metacarpophalangeal finger joint (knuckle). A first anchor element 106 is adapted to be positioned adjacent a jointed appendage of a user at a first position. Preferably, the spring member 104 is movable though the first anchor element 106 so that it may travel and be elongated without resistive force when the finger is bent. Anyone skilled in engineering can readily design many anchoring schemes that will permit a free length of the spring material 104 to slide as needed when the finger is bent to the position show in FIG. 1B.

As shown in FIGS. 1A and 1B, the first anchor element 106 is positioned beyond the wrist 105 so that the bending torsion of the spring member 104 might, if needed, be used to assist in straightening the wrist. Alternatively, the first anchor element 106 may stop just short of the wrist, adjacent to the palm, as shown, for example, in FIG. 2. The first anchor element 106 may be affixed to the hand and/or wrist by means of an elastic strap, VELCRO® strap, or the like. In addition, the first anchor element 106 may be built into the structure of a glove, or glove-like appliance.

The spring member 104 is also anchored by a second anchor element 108, which is positioned about the jointed appendage at a second position. The jointed appendage is located between the first anchor element 106 and the second anchor element 108. In the exemplary embodiment, the second anchor element 108 is placed at the tip of the finger. Preferably, the spring member 104 is fixedly secured to the second anchor element 108 to statically constrain the end of the spring member 104 to the tip of the finger. However, importantly, the spring member 104 should be unrestrained at the joint.

An intermediary support device is disposed between the first anchor element 106 and the second anchor element 108 so as to prevent the spring member 104 from contacting the joint(s) of the user. In the exemplary embodiment, the intermediary support device includes a series of pads 110, 114, and 118 disposed along the length of the finger 102. The pads 110, 114, and 118 may be held by means of a glove, strap, or the like. Associated with each pad 110, 114, and 118 are bushings 112, 116, and 120. The bushings 112, 116, and 120 provide low friction guidance of the spring member 104 as is slides forward and backwards through the first anchor element 106, as the finger is bent and straightened. Preferably, the pads are disposed between the joints 126, 127, and 128. However, the number and location of pads can vary, depending upon application and design preference. Likewise, additional pads, such as pad 122, may be provided without a bushing, depending upon application and design preference. Accordingly, the intermediary support device provides support along non-joint positions of the appendage so that the spring member 104 is unable to apply any significant forces to the joints of the appendage. As such, the bushings 112, 116, and 120 should be built in a manner to straighten and elevate the spring member 104 to prevent contact with the fingers.

In operation, the movement device 10, as shown in FIGS. 1A and 1B is typically worn by a person who has the ability to clench the hand into a first but cannot open the hand. The bending force of the spring element is sufficient to straighten the finger and hold it straight against the relaxed muscles of the user. From this open position, the user is now able to use the muscles of the hand to bend, close, or position one or more fingers as needed. However, the spring member 104 may be designed for the opposite scenario, where a person has the ability open the hand, but not close the hand into a fist.

Figure 7:
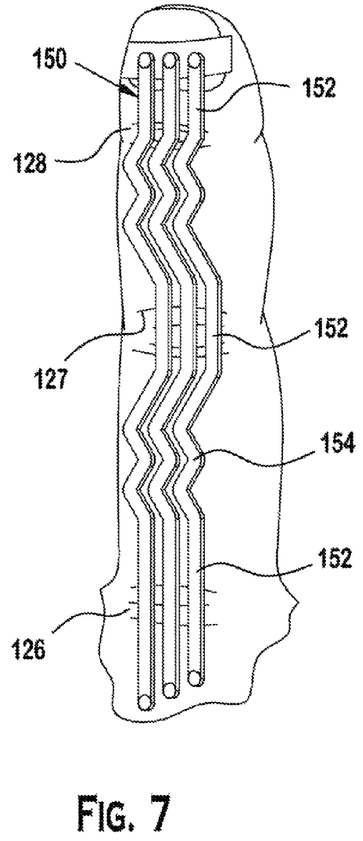
FIG. 7 is a top plan view of a nested rod configuration of the spring member according to features of the present invention.

In the exemplary embodiment, the spring member 104 is a flat material possessing the ability to bend through 90 degrees around radii of about 0.375 inches, more or less, without suffering permanent deformation. However, other radii are possible, depending upon application and design preference. With reference to FIG. 7, the spring member 104 can be comprised of one or more nested rods 150 disposed in a vertically flat arrangement. By using multiple rods of actuator material, the total force of the spring member 104 can be adjusted by adding or removing rods or layers thereby permitting the device to accommodate differences between users and changes that might occur over time with a given user. As shown in FIG. 7, the nested rods 150 include straight portions 152 at the joint locations 126, 127, and 128, and zigzag portions 154 at the non-jointed locations above the pads (not shown).

Figure 8:
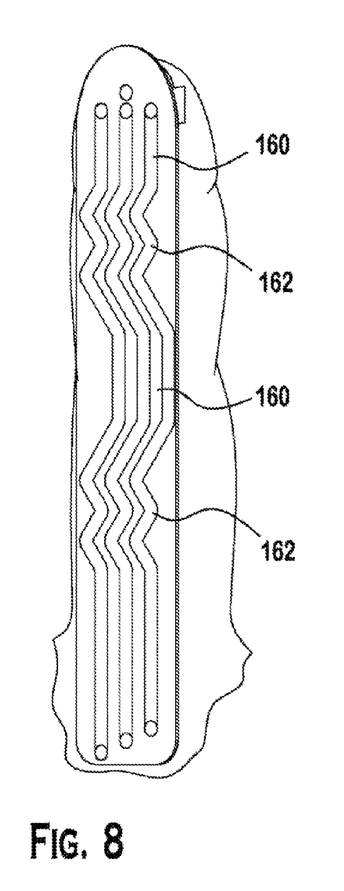
FIG. 8 is a top plan view of an etched blade configuration of the spring member according to features of the present invention.

In addition, as shown in FIG. 8, the spring member 104 may be a single flat blade, that is etched so that it includes straight portions 160 and zigzag portions 162. In particular, the blade may be etched into the same pattern as the nested rods 150 by including but not limited to laser etching, water etching, and/or EDM. As such, the straight portions 160 are disposed above the joint locations 126, 127, and 128, and the zigzag portions 162 are disposed above the non-jointed locations above the pads (not shown).

The spring member 104 may also be made from multiple layers of flat material. In this way, the number of layers and thickness of each layer is applicable to the total spring force and permits thinner, more flexible material to be used to endure bending through 90 degrees without permanent deformation.

Because the thickness, width and number of the spring members are used to determine the bending force applied at a particular joint, sections of the actuator material between the joint can be configured in a variety of ways. The actuator material can have other materials affixed to its surface to provide stiffness between the finger sections or at the joints if this should prove useful or necessary for a particular patient. The actuator material can also be located on the inside of the hand, running under the finger instead of on top in which case obvious changes in the configuration of the mounting bushings and other associated components are required. Another novelty of the movement device of the present invention is that bending forces are employed instead of tension forces to accomplish motion.

The assembly of components shown in FIGS. 1A and 1B schematically represents a novel embodiment of SMA material used in a bending mode rather than elongation and contraction, such application of SMA being unique in addressing the problem of finger manipulation. One skilled in design can readily appreciate, without further elaboration of detail, that the components illustrated can be built into a glove or similar easy-to-wear and esthetically pleasing device. Similarly a wide variety of fixtures can be made to permit the device to be worn without the fabric of a glove, one such concept being a simple arrangement of rings through which the fingers can slide and onto which are affixed the components of the invention shown.

With reference to FIGS. 2-6, another exemplary embodiment of the present invention is illustrated. With specific reference to FIG. 2, the hand extension/flexion device 200 includes a glove body 202 for positioning around a hand of a user. The glove body 202 may include one or more finger portion 204 for positioning about one or more fingers of a user, and a thumb portion 206 for positioning about a thumb of a user. At least one spring member 208 is adapted to be positioned along the length of a finger portion 204, and anchored between a first anchor element 106 and a second anchor element 210. In the preferred embodiment, there are five spring members 208, one for each of the four finger portions 204 and one thumb portion 206. However, the number of spring members used on particular fingers and thumb will depend upon the user of the device, and what the device is being used for.

As described above, the spring member may be a flat blade, but can also be comprised of one or more nested rods 150, as shown in FIG. 7. In addition, as shown in FIG. 8, the spring member 104 may be a single flat blade, that is etched so that it includes straight portions 160 and zigzag portions 162. In particular, the blade may be etched into the same pattern as the nested rods 150 by including but not limited to laser etching, water etching, and/or EDM. As such, the straight portions 160 are disposed above the joint locations 126, 127, and 128, and the zigzag portions 162 are disposed above the non-jointed locations above the pads (not shown). The spring member 104 may also be made from multiple layers of flat material. In this way, the number of layers and thickness of each layer is applicable to the total spring force and permits thinner, more flexible material to be used to endure bending through 90 degrees without permanent deformation.

Figure 2:
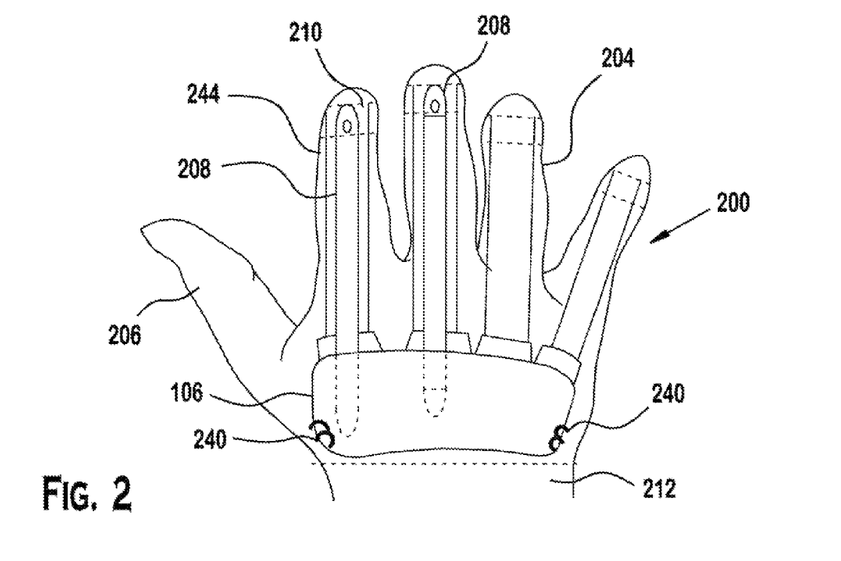
FIG. 2 illustrates is a top plan view of the spring members positioned on the glove according to the features of the present invention.
Figure 4:
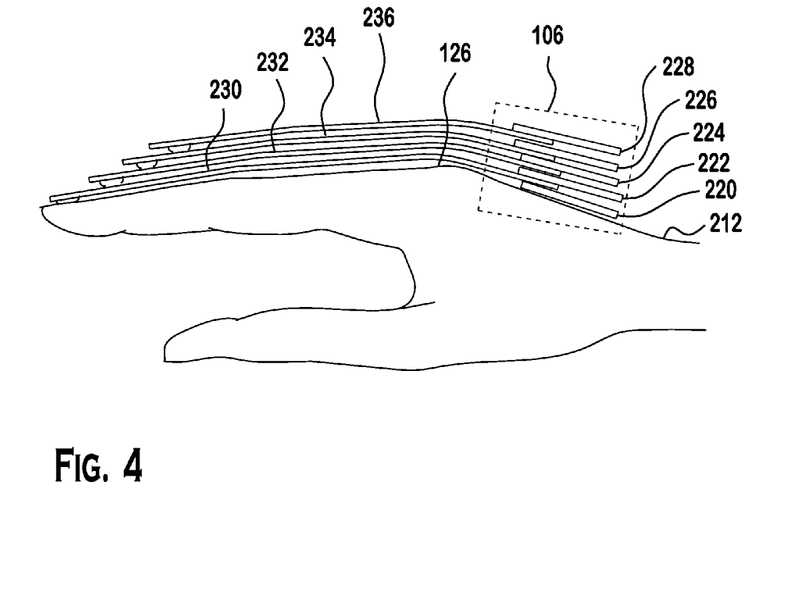
FIG. 4 illustrates a perspective view of an exemplary product according to the features of the present invention.

With reference to FIGS. 2 and 4, the first anchor element 106 is preferably located between the wrist 212 and the metacarpophalangeal finger joints 126 (see FIGS. 1A and 1B). However, other locations are possible. Preferably, the first anchor element 106 is made from a thin TEFLON® coated fiberglass, KAPTON®, or the like, having a plurality of layers, wherein the spring members are interleaved within the plurality of layers 220, 222, 224, 226, and 228. In particular, a first spring member 230 is interleaved between a base layer 220 and adjacent layer 222. A second spring member 232 is interleaved between the layer 222 and layer 224. A third spring member 234 is interleaved between the layer 224 and 226, and a fourth spring member 236 is interleaved between layers 226 and 228. In this way, the fingers and corresponding blades are capable of splaying without adjacent spring members colliding with one another.

Figure 3:
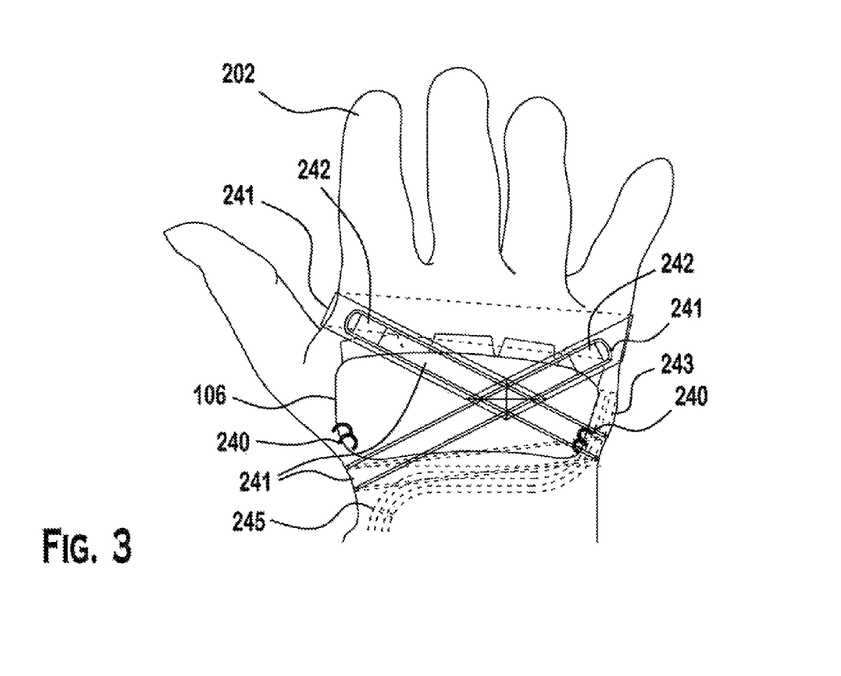
FIG. 3 illustrates is a top plan view of the glove body with the first anchor element according to the features of the present invention.

The first anchor element 106 may also include a guard plate disposed on the top layer 228 to prevent the blades from penetrating through the first anchor element 106. To keep the first anchor element 106 secured on the glove, a set of mechanical fasteners 240 may be affixed on ends of the first anchor element 106. In addition, as shown in FIG. 3, a series of straps 241 may be used to secure the first anchor element 106 to the glove body 202. A VELCRO® pad 242 may be used for easy tightening and loosening. Optionally, a zipper 243 may be included that allows access to the internal components of the device 200. A hand stitched tack 245 may also be included to prevent the user from routinely uncovering the first anchor element 106. However, it should also be understood that the first anchor element 106 may take other forms, such as an adjustable strap or the like, as shown, for example, in FIGS. 1A and 1B.

As shown in FIG. 2, the spring element 208 may be a flat blade that is affixed to the second anchor element 210. In the exemplary embodiment, the flat blade includes aperture 212, which may be sewn to a piece of material, such as lanyard material, affixed to the tip of the finger portion of the glove. However, the blades may be secured in any other way though numerous types of complimentary mechanical devices. For example, blades may also include an aperture at its distal end, whereby the flat blade may be riveted or sewn to the glove body.

Figure 5:
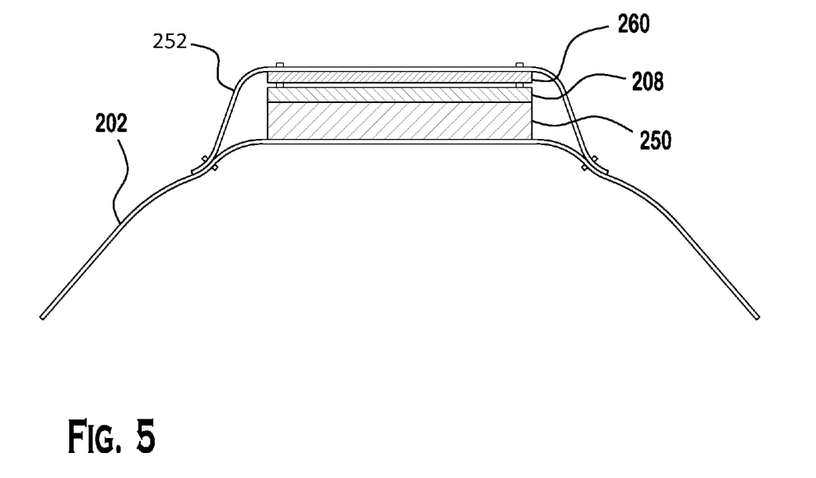
FIG. 5 illustrates a cross sectional view of a finger portion of the exemplary product according to features of the present invention.
Figure 6:
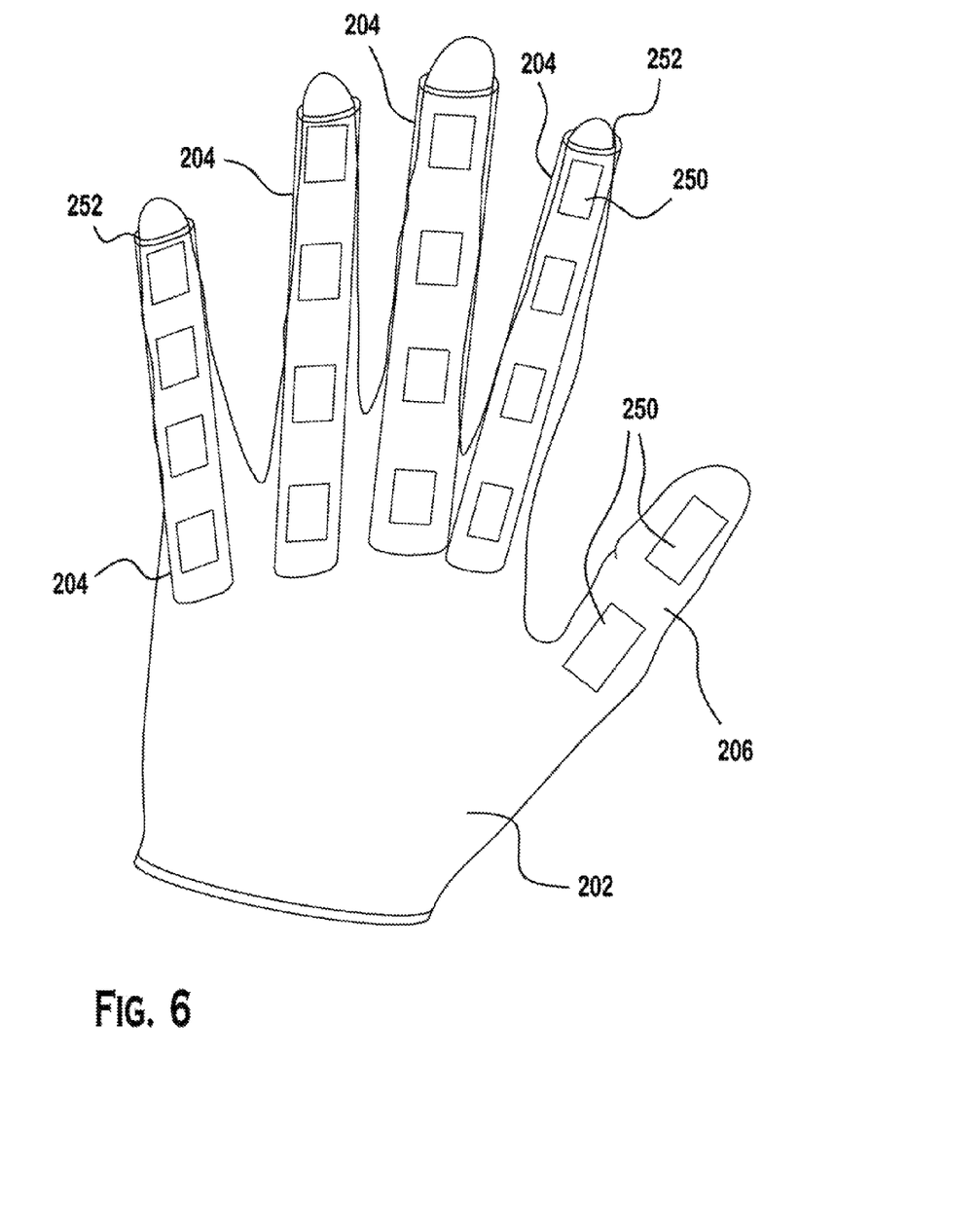
FIG. 6 is a perspective view of the exemplary glove without the spring member according to features of the present invention.

Similar to the embodiment shown with regard to FIGS. 1A and 1B, the hand extension/flexion device 200 of FIGS. 2-6 includes an intermediary support device disposed between the first anchor element 106 and the second anchor element 210 so as to prevent the spring member 208 from contacting the knuckles of the user. As shown in FIG. 6, the intermediary support device includes a series of pads 250 which cushion the spring member 208. In addition, the intermediary support device includes at least one channel 252 for restraining the spring element 208. However, there may be numerous channels 252 per finger or other guiding/restraining mechanisms, depending upon application and design preference. Preferably, the channel is made from fabric, but may be made from any flexible, yet durable material, capable of restraining and guiding the spring element 208, while also allowing the device to flex and straighten.

As shown in FIG. 6, the pads are disposed directly on the glove body 202, and are preferably applied when customizing the glove to a hand of a user. For example, the pad may be applied to the glove in a long strip, with portions at the knuckle removed when a user flexes his hand. As shown in FIG. 6, there are four pads disposed along each finger portion 204, and two pads disposed along the thumb portion 206 of the glove body 202. Pads of varying thickness may be used, depending upon application and design preference. The glove 202 may be custom made for each user, and disposable. Once the glove body is made with pads and channels attached, the spring members may be added and anchored onto the glove body.

With reference to FIG. 5, a cross section view of the device along a finger portion of the glove body 202 is illustrated. As shown therein, a pad 250 is disposed above the glove body 202, so as to cushion the spring element 208 and follow the contour of the glove body 202. Optionally, a piece of material 260, such as MYLAR®, may be positioned between the channel 244 and spring member 208 to minimize friction between the channel 252 and the spring member 208. The MYLAR® may be stitched or bonded to the inside fabric of the channel. Nevertheless, the channel may be made of a sufficiently smooth material so that friction is minimized between the spring element 208 and the channel 252. The padding 250 may be razor cut, peel away padding. When a fist of the user is formed, a clinician can remove sections of the padding conflicting with the knuckles.

Figure 9:
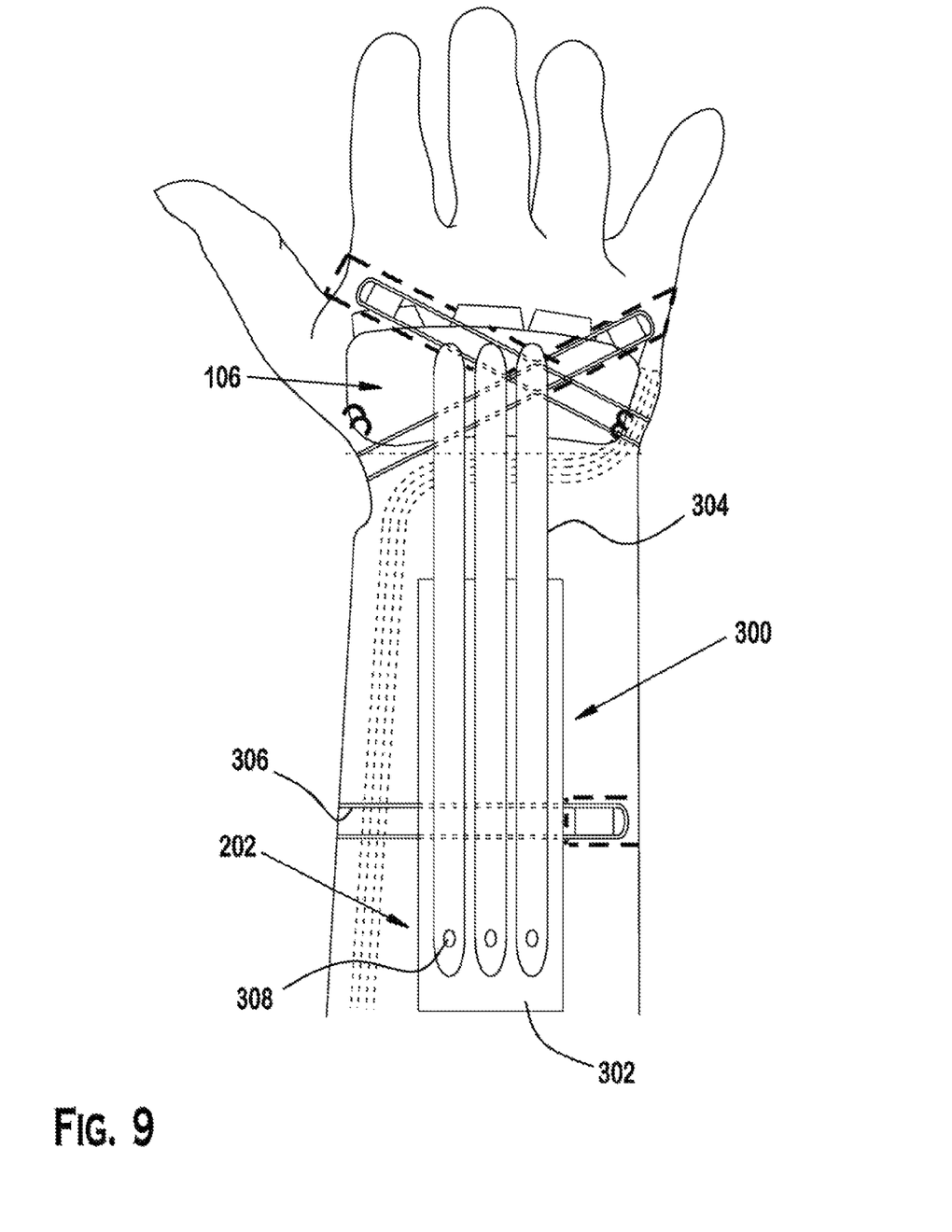
FIG. 9 is a top plan view of a wrist flexion device to be used with the hand movement device according to features of the present invention.

With reference to FIG. 9, an alternative embodiment showing a wrist flexion device 300 to be used in connection with the hand extension/flexion device 200 is illustrated. As shown in FIG. 9, there are a series of channels 302 disposed on the forearm or gauntlet of the glove body 202. A number of blades 304 are disposed within the channels 302 and extend from a lower part of the forearm across the wrist onto the opisthenar (back of the hand) into the first anchor element 106. Preferably, 3 or 4 blades are used, but may be any number of blades depending upon application and design preference. Preferably, the blades are preformed with a 90-degree bend of radius at two inches to allow for full dorsiflexion of the wrist. As the patient will typically have the ability to peform palmar flexion, the wrist can be extended to any desired angle. The actuator blades 304 are anchored at the distal end of the blade relative to the wrist by rivets 308 or the like; the proximal end is left free to slide beneath the guide plate stack or first anchor device 106 to allow for ulnar and radial deviation of the wrist. Preferably, a VELCRO™ strap 306 or the like is used to secure the blades 304 from upward movement. The thumb may be configured in the same fashion.

An advantage of the present invention is that by using the bending force actuator, as opposed to the tensile force actuators of all known prior methods, there is no compressive load applied to the joints by the device. At the same time, there is no need for elaborate external cantilevers, scaffolds, tension wires, pulleys, ratchets, motors, or other means to accomplish the objectives of the invention. Thus the invention results in a desired and needed convenient, simple, robust, and inconspicuous device.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

The invention claimed is:

1. A disposable glove for use in a hand extension/flexion device, comprising:
   a glove body for positioning around a hand of a user;
   a series of pads affixed to a surface of at least one finger portion of the glove body, said pads being positioned between joints of the finger;
   a channel defined by the glove disposed around said pads, said channel also configured for housing a spring member adapted to exert bending forces in opposition to working muscles of the user to straighten or flex joints of the finger; and
   a first anchor element for receiving a proximal end of the spring member and a second anchor element adapted for receiving a distal end of the spring member, wherein the first anchor element is configured to permit lateral and longitudinal movement of a first, free end of the spring member, wherein the spring member is fixedly secured to the second anchor element at a second end of the spring member so as to statically constrain the second end of the spring member to the top of the finger.

* * * * *